United States Patent [19]

Battenfield

[11] Patent Number: 5,730,749
[45] Date of Patent: Mar. 24, 1998

[54] CARPAL TUNNEL SURGERY INSTRUMENTS

[76] Inventor: Harold L. Battenfield, 4414 S. Zunis, Tulsa, Okla. 74105

[21] Appl. No.: 574,454

[22] Filed: Dec. 15, 1995

[51] Int. Cl.$^6$ .................................................. A61B 17/34
[52] U.S. Cl. ................................................ 606/167; 606/170
[58] Field of Search ........................... 128/898; 606/167, 606/170, 171, 172, 180, 186; 604/22; 600/104, 106, 114, 125, 127

[56] References Cited

U.S. PATENT DOCUMENTS

| | | | |
|---|---|---|---|
| 4,962,770 | 10/1990 | Agee et al. | 606/170 |
| 5,273,024 | 12/1993 | Menon et al. | 600/114 |
| 5,282,816 | 2/1994 | Miller et al. | 606/167 |
| 5,318,582 | 6/1994 | Chow | 606/170 |
| 5,323,765 | 6/1994 | Brown | 606/170 |
| 5,325,883 | 7/1994 | Orr | 606/172 |
| 5,346,503 | 9/1994 | Chow | 606/170 |
| 5,352,233 | 10/1994 | Anis | 606/167 |
| 5,356,419 | 10/1994 | Chow | 606/170 |
| 5,366,465 | 11/1994 | Mirza | 606/167 |
| 5,387,223 | 2/1995 | Agee et al. | 606/167 |
| 5,425,355 | 6/1995 | Kulick | 606/17 |
| 5,458,611 | 10/1995 | Resnick et al. | 606/167 |

*Primary Examiner*—Michael Buiz
*Assistant Examiner*—Patrick W. Rasche
*Attorney, Agent, or Firm*—Frank J. Catalano; Scott R. Zingerman

[57] ABSTRACT

Instruments for use in endoscopic carpal tunnel surgery include a cannula having a diameter suitable for passage in the carpal tunnel, a diametrically narrowing open tip to facilitate entry into the carpal tunnel and a matted interior surface to maximize visual clarity of the carpal tunnel display, an obturator having a diameter suitable for passage in the cannula end, a plow shaped tip which laterally shifts tendons and nerves from its path as the tip is passed in the carpal tunnel and a sway-back portion proximate the tip which maximizes the efficiency of the tip as it plows through the carpal tunnel tendons and nerves and a rasp having a rod of diameter suitable for passage in the cannula, a roughened face on an upwardly tapering trapezoidal cross-section tip for guiding penetration of the tip through the longitudinal slot in the cannula but limiting penetration of the tip therethrough, and a bend in the rod so that the roughened face of the tip is in substantially flush alignment with the ligaments when the tip is external of the cannula. Using these instruments, endoscopic carpal tunnel surgery is an approximately half-hour procedure requiring two one centimeter incisions. Resistance to passage of the instruments and the possibility of damage to tendons and nerves is reduced in comparison to known instruments. The resulting recovery period is in a range of two to three weeks. This smaller mass passed through the confines of the carpal tunnel and further compressing the median nerve results in markedly reduced post-surgical complaints.

16 Claims, 3 Drawing Sheets

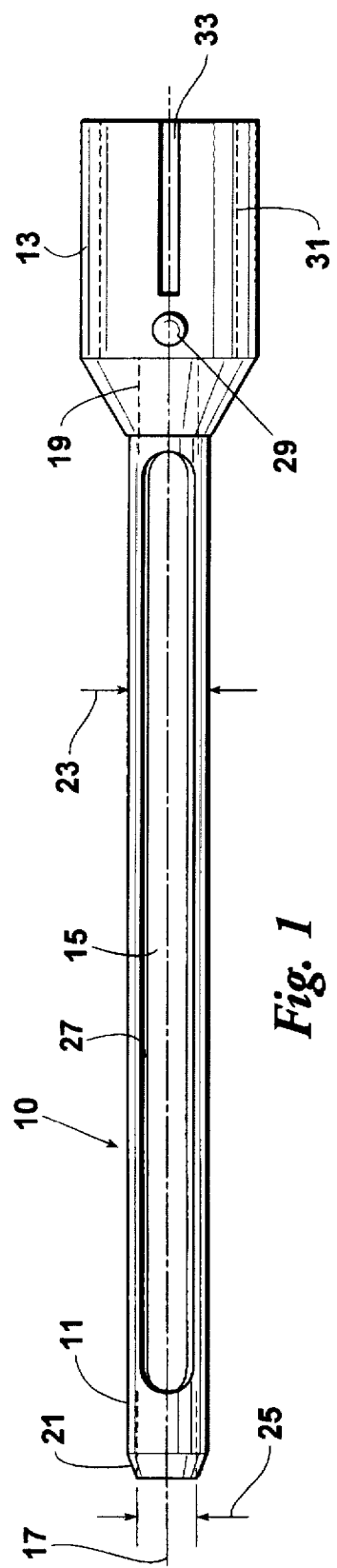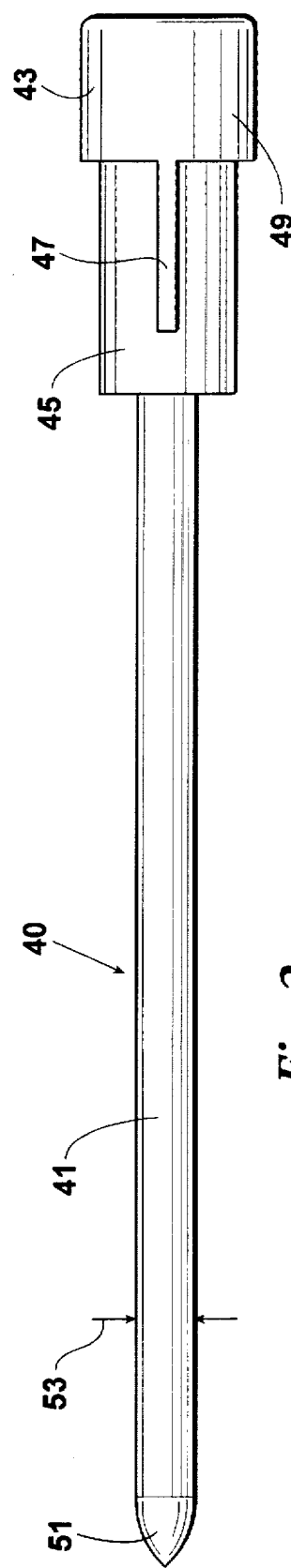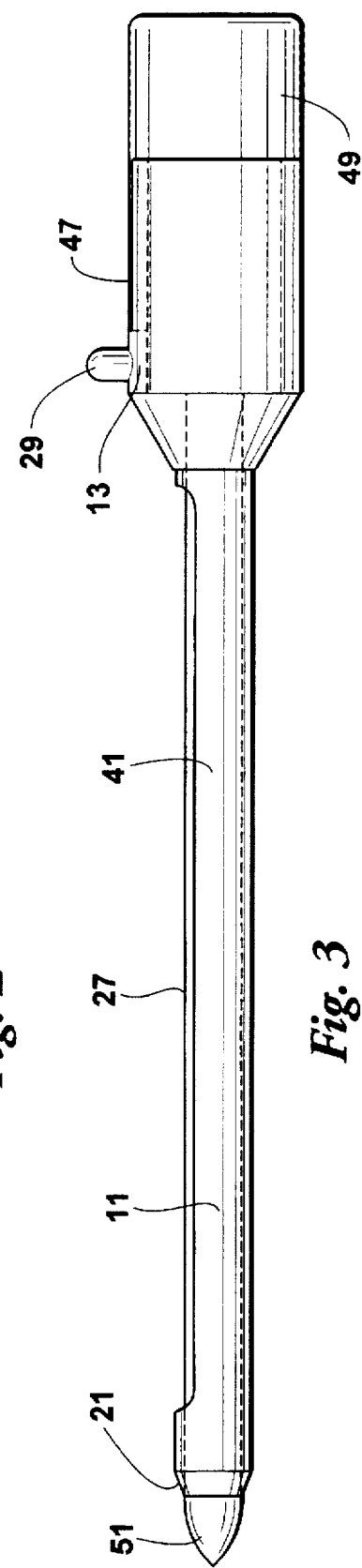

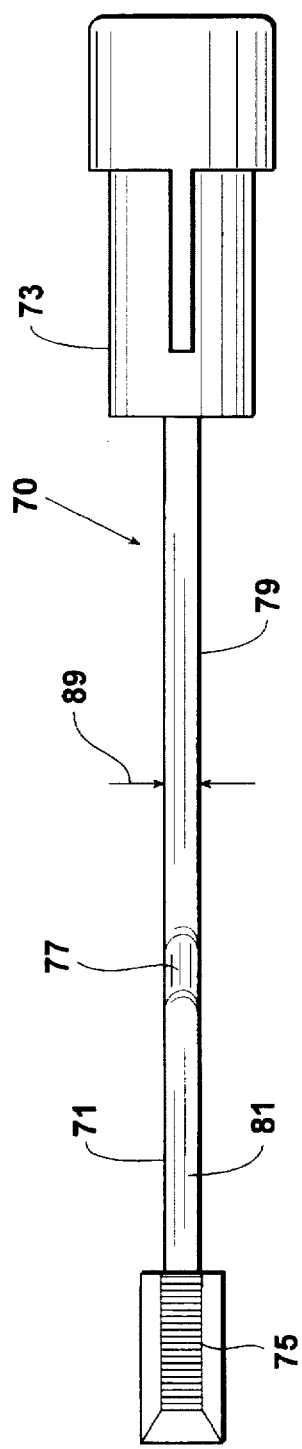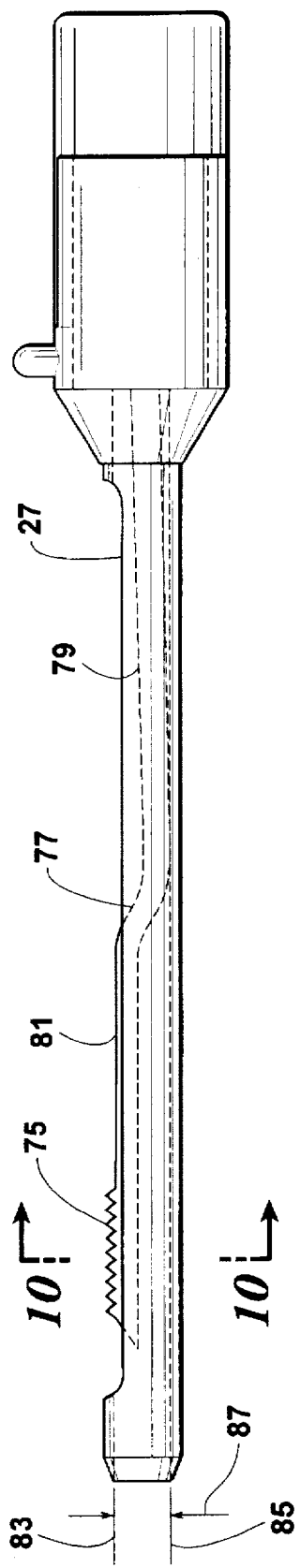

CARPAL TUNNEL SURGERY INSTRUMENTS

BACKGROUND OF THE INVENTION

This invention relates generally to endoscopic surgery and more particularly concerns instruments used in carpal tunnel endoscopic surgery.

Surgery to decompress the carpal tunnel and therefore the pressure on the median nerve has been known for many decades. The longest known procedure typically involves an incision ranging from two to five inches in length and requiring as much as six weeks to heal. Since the introduction of endoscopic surgery, the procedure involves only one or two relatively small incisions, resulting in significantly faster recovery. However, existing endoscopic instruments produce new and unanticipated problems. Such instruments, when forced into the carpal tunnel as a step in the surgical procedure before decompression, result in new postoperative complaints of pain or numbness, especially in the middle and ring fingers, in a high percentage of existing endoscopic carpal tunnel surgery patients. It is estimated that fifteen to twenty percent of carpal tunnel surgery patients proffer such complaints after use of these known instruments.

It is, therefore, an object of this invention to provide instruments specifically suited to carpal tunnel endoscopic surgery. It is also an object of this invention to provide a carpal tunnel cannula of diameter suited for insertion into the carpal tunnel. Another object of this invention is to provide a cannula having a diametrically narrowing tip to facilitate its passage into the carpal tunnel. A further object of this invention is to provide a cannula having a matted interior surface to enhance visual display of the surgical area. Another object of this invention is to provide an obturator having a plow shaped tip facilitating passage of the obturator tip in the carpal tunnel. In another object of this invention is to provide a rasp specifically suited for manipulation in a carpal tunnel cannula. It is also an object of this invention to provide a rasp configured to guide its toughened surface through the cannula slot to the ligament to be treated. Another object of this invention is to provide a rasp configured so as to limit the distance to which the roughened surface may be radially extended through the cannula slot. And it is an object of this invention to provide a rasp configured to permit longitudinal alignment of the roughened surface with the ligament to be treated.

SUMMARY OF THE INVENTION

In accordance with the invention, several cooperable instruments are provided for use in endoscopic carpal tunnel surgery.

A cannula with a diameter suitable for passage in the carpal tunnel has an elongated longitudinal slot extending from a point proximate its grip end to a point proximate a diametrically narrowing open tip at its other end. Preferably, the cannula has a tube diameter of less than 5 millimeters with a narrowest tip diameter of not less than 4 millimeters. The grip has a visual indicator of the angular orientation of the cannula slot fixed to it so that the alignment of the slot with the ligament can be assured when the cannula tube is fully inserted into the carpal tunnel. The slotted tube has a matted interior surface to maximize visual clarity of the carpal tunnel display. Otherwise, the small diameter cannula is in such proximity to the light source that glare makes visualization impossible.

An obturator having a rod of diameter suitable for passage in the cannula has a grip fixed to one end and a plow shaped tip on its other end. The length of the rod is such that, when the obturator is fully inserted into the cannula, the plow-shaped tip extends beyond the forward end of the cannula to laterally shift tendons and nerves from its path as the tip is passed in the carpal tunnel. Preferably, the plow shaped tip has a substantially inverted triangular cross-section taken transversely along its longitudinal axis. The cross-sections have decreasing bases substantially in a common plane and decreasing heights tapering upwardly toward a forwardmost portion of the tip, giving the tip the appearance of the bow of a boat. The flair of the tip rises above and spreads the tendons simultaneously, much like a bow functions in the water.

A rasp of diameter suitable for passage in the cannula has a grip fixed to its rear end and a tip with a roughened upper face on its forward end. The roughened face width is less than the width of the longitudinal slot in the cannula tube. The tip has an upwardly tapering trapezoidal cross-section taken transversely along a longitudinal axis of the rasp so that the tapered trapezoidal sides guide penetration of the tip through the longitudinal slot in the cannula tube. However, the base of the trapezoidal cross-section is greater than the width of the slot in the cannula tube so as to limit penetration of the tip therethrough. Thus, synovium can be effectively removed using controlled pressure with minimal risk of over-rasping. Preferably, the rasp is bent to provide forward and rearward segments having displaced parallel longitudinal axes, the bend preferably being proximate a midpoint of the rasp and the displacement being such that, when the rearward segment is substantially concentrically aligned within the cannula tube, the roughened upper face of the tip is external of the cannula slot and in substantially flush alignment with the ligament. Preferably, the rasp is designed to grip the cannula grip to assure registration of the roughened upper face of the rasp with the slot in the cannula tube when the rasp is fully inserted into the cannula.

Using the above-described instruments, endoscopic carpal tunnel surgery is an approximately half-hour procedure requiring two one centimeter incisions. This smaller mass passed through the confines of the carpal tunnel and compressing the median nerve results in greatly reduced new post-surgical complaints. Resistance to passage of the instruments and the possibility of damage to tendons and nerves is reduced in comparison to known instruments. The resulting recovery period is in a range of two to three weeks.

BRIEF DESCRIPTION OF THE DRAWINGS

Other objects and advantages of the invention will become apparent upon reading the following detailed description and upon reference to the drawings in which:

FIG. 1 is a top plan view of a preferred embodiment of a cannula for use in carpal tunnel endoscopic surgery;

FIG. 2 is a top plan view of a preferred embodiment of an obturator for use in carpal tunnel endoscopic surgery;

FIG. 3 is a side elevation view illustrating the obturator of FIG. 2 fully inserted in the cannula of FIG. 1;

FIG. 8 is a top plan view of a preferred embodiment of a rasp for use in carpal tunnel endoscopic surgery;

FIG. 9 is a side elevation view of the rasp of FIG. 8 fully inserted in the cannula of FIG. 1.

Figure 5:
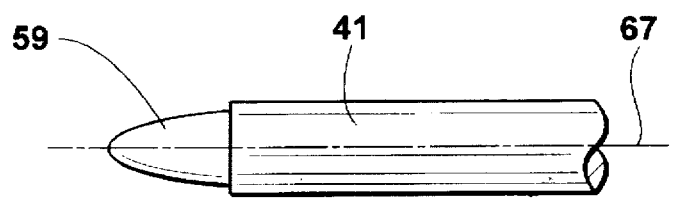
FIG. 5 is a top plan view of the obturator tip of FIG. 4.
Figure 7:
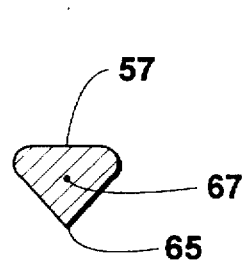
FIG. 7 is a cross-sectional view taken along line 7—7 of FIG. 4.
Figure 4:
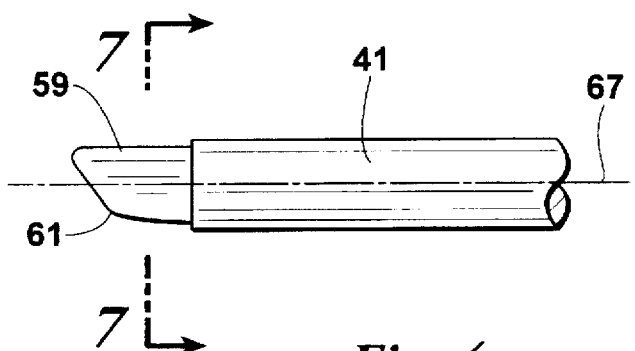
FIG. 4 is a side elevation view of a preferred embodiment of a plow tip for an obturator used in carpal tunnel endoscopic surgery.
Figure 6:
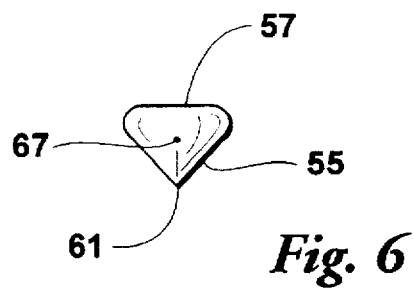
FIG. 6 is a front elevation view of the obturator tip of FIG. 4.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION OF THE INVENTION

Turning first to FIG. 1, a preferred embodiment of a cannula 10 for use in carpal tunnel endoscopic surgery is illustrated. An elongated tube 11, preferably of stainless steel but of any surgically suitable material, has a grip 13 fixed to its rear end. The tube 11 defines a first instrument passage 15 aligned on its longitudinal axis 17 and the grip 13 has an instrument passage 19 extending longitudinally through it and aligned with the passage 15 in the tube 11. The front end of the tube 11 has a diametrically narrowing open tip 21. The overall diameter 23 of the tube 11 is selected so as to be relatively easily inserted into a carpal tunnel. The diameter 23 of the tube 11 will generally be less than 5 millimeters and typically approximately 4.75 millimeters while the narrowest diameter 25 of the open tip 21 will typically be in the order of 4 millimeters. An elongated longitudinal slot 27 is provided in the top of the cannula 20 extending from a point proximate the front of the grip 13 to a point proximate the narrowing open tip 21. A knurl 29 or other indicator is fixed to the outer portion of the grip 13, preferably in longitudinal alignment with the slot 27, so as to provide a visual indication of the angular orientation of the slot 27 when the tube 11 is fully inserted into the carpal tunnel. As shown, the grip 13 may also be provided with a cylindrical seat 31 into which the grips of other surgical instruments may be inserted as will hereinafter be explained. In addition, a slot 33 may be provided, preferably longitudinally aligned with the knurl 29, to facilitate angular orientation of such other surgical instruments in the cannula 10. It is preferred that the interior surface of the tube 11 have a matted surface to enhance the quality of the visual display of the interior of the cannula 10. The grip 13 will preferably be made of Delrin®.

Looking now at FIG. 2, an obturator 40 for use with the cannula 10 illustrated in FIG. 1 is shown. The obturator 40 consists of an elongated rod 41 having a grip 43 at a rear end thereof. As shown, the grip 43 has a cylindrical forward portion 45 with a key 47 longitudinally aligned on its perimeter and extending to a base cylindrical portion 49. As can best be seen in FIG. 3, the grip 49 is configured to cooperate with the grip 13 of the cannula 10 with the key 47 inserted into the slot 33 on the cannula 10 until the base portion 49 of the obturator grip 43 abuts the cannula grip 13. As shown, the rod 41 has a plow shaped tip 51 at its forward end and the length of the rod 41 is such that, when the obturator 40 is fully inserted into the cannula 10, the tip 51 extends forwardly of the open tip 21 of the cannula 10. The plow shaped tip 51 of FIGS. 2 and 3 is similar in contour to presently known larger obturators. However, the diameter 53 of the rod 41 is substantially equal to the diameter of the narrowest portion 25 of the cannula tip 21. Thus, the extension of the plow shaped tip 51 combined with the tapered open tip 21 of the cannula provides a substantially smooth surface for penetration of the carpal tunnel without damage to tendons and nerves in its path. Preferably the obturator rod 41 will be of stainless steel and the grip 43 of Delrin®.

Turning now to FIGS. 4 through 7, a specially preferred embodiment of the plow tip of the obturator 40 is illustrated. In this embodiment, cross-sections of the tip of the rod 41 are shaped substantially like inverted triangles 55, the top portion of the tip being the bases 57 of the triangles 55 lying in a common plane 59. However, approaching the forward most portion of the tip, the bases 59 narrow as can best be seen in FIG. 5 while the distance from the bases 59 to their apexes 61 decreases, as can best be seen in FIG. 4. As a result, instead of the bullet like shape of the plow tip 51 illustrated in FIG. 2, the preferred plow tip has the appearance of the bow of a boat and functions in similar fashion, the flair of the tip rising above and spreading the tendons and nerves as the tip penetrates the carpal tunnel.

Figure 10:
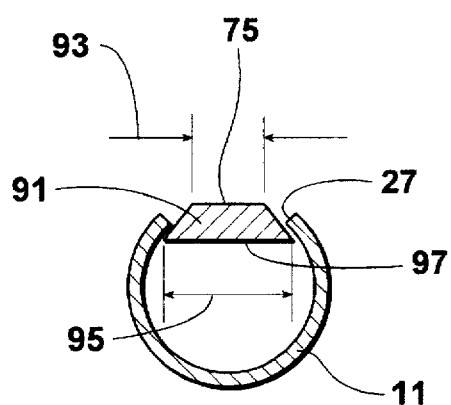
FIG. 10 is a cross-sectional view taken along the line 10—10 of FIG. 9.

Looking at FIG. 8, a preferred embodiment of a rasp 70 for use in carpal tunnel endoscopic surgery is illustrated. The rasp 70 has an elongated rod 71 having a grip 73 which, as shown, is in all respects similar to the grip 43 on the obturator 40 illustrated in FIG. 2. The forward end of the rasp 70 has an upper roughened or toothed surface 75. As can best be seen in FIG. 9, the rod 71 has a bend 77 proximate its midpoint dividing the rod 71 into a rearward segment 79 and a forward segment 81. As shown, the longitudinal axis 83 of the forward segment 81 is displaced from the longitudinal axis 85 by a distance 87 such that, when the longitudinal axis 85 of the rear segment 79 is aligned with the longitudinal axis 17 of the cannula 10, the roughened face 75 of the rasp 70 extends above the slot 27 of the cannula 10 so as to be substantially flush with the ligament to which it will be applied. The diameter 89 of the rod 71 is therefore selected to provide maximum strength to the rasp 70 while permitting suitable passage thereof in the cannula 10. As can best be seen in FIG. 10, the forward end of the rod 71 is of substantially trapezoidal cross section with the roughened face 75 being the shorter parallel side of the trapezoid 91. The width 93 of the roughened face 75 is less than the width of the slot 27 in the cannula tube 11. The width 95 of the base of the trapezoid 91 is greater than the width of the slot 27 in the cannula tube 11. Thus, the sloping sides of the trapezoid 91 guide the passage of the roughened face 75 of the rasp 70 through the slot 27 in the cannula tube 11, while the wider base 97 limits the distance to which the roughened face 75 can extend above the slot 27 in the cannula tube 11. Thus, the displaced configuration of the rod 71 and the trapezoidal configuration of its forward end help to assure that the roughened face 75 can be applied in flush relationship to the ligament with minimized risk of over rasping. Preferably, the rod 71 will be of stainless steel and the grip 73 of Delrin®.

A standard 4 mm scope can be placed within the cannula of the present invention, and the scope and the cannula of the present invention can be placed within the smallest existing instruments.

Thus, it is apparent that there has been provided, in accordance with the invention, instruments for carpal tunnel endoscopic surgery that fully satisfy the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. For use with a carpal tunnel cannula, an obturator having an elongated rod of diameter suitable for passage in the cannula, said rod having a grip fixed to a rear end thereof and a tip on a forward end thereof, said tip having substantially inverted triangular cross-sections taken transversely to a longitudinal axis of said rod, said cross-sections having decreasing bases substantially in a common longitudinal plane and decreasing heights tapering upwardly toward a forwardmost portion of said tip and said rod being of length such that, when said obturator is fully inserted into the cannula, said tip extends beyond a forward end of said cannula for lateral shifting of tendons and nerves from a path thereof as said tip is passed in the carpal tunnel.

2. For use with a carpal tunnel cannula, a rasp having an elongated rod of diameter suitable for passage in the cannula, said rod having a grip fixed to a rear end thereof and a tip having a roughened upper face on a forward end thereof, said face having a width less than a width of a longitudinal slot in the cannula, said tip having an upwardly tapering trapezoidal cross-section taken transversely to a longitudinal axis of said rod for guiding penetration of said tip through the longitudinal slot in the cannula, a base of said trapezoidal cross-section being greater than the width of the slot in the cannula for limiting penetration of said tip therethrough.

3. A rasp according to claim 2, said grip having means fixed thereon for keying with a cooperable means on the cannula to assure registration of said roughened upper face of said rasp with the slot in the cannula when said rasp is fully inserted into the cannula.

4. For use with a carpal tunnel cannula, a rasp having an elongated rod of diameter suitable for passage in the cannula, said rod having a grip fixed to a rear end thereof and a tip having a roughened upper face on a forward end thereof, said face having a width less than a width of a longitudinal slot in the cannula, said tip having an upwardly tapering trapezoidal cross-section taken transversely to a longitudinal axis of said rod for guiding penetration of said tip through the longitudinal slot in the cannula, said rod being bent to provide forward and rearward segments having displaced parallel longitudinal axes.

5. A rasp according to claim 4, said rod being bent proximate a midpoint thereof.

6. A rasp according to claim 4, said displacement being such that, when said rearward segment is substantially concentrically aligned within the cannula, said roughened upper face is external of said cannula.

7. For use in endoscopic carpal tunnel surgery, a combination of instruments comprising:

a cannula having an elongated tube of diameter suitable for passage in the carpal tunnel, said tube defining a first instrument passage longitudinally therein and having a grip fixed to a rear end thereof, said cannula grip having a second instrument passage extending therethrough and aligned with said first instrument passage, and an elongated longitudinal slot extending from a point proximate a forward end of said cannula grip to a point proximate a diametrically narrowing open tip at another end thereof; and an obturator having an elongated rod of diameter suitable for passage in said cannula, said rod having a grip fixed to a rear end thereof and a on a forward end thereof, said tip having substantially inverted triangular cross-sections taken transversely to a longitudinal axis of said rod, said cross-sections having decreasing bases substantially in a common longitudinal plane and decreasing heights tapering upwardly toward a forwardmost portion of said tip and said rod being of length such that, when said obturator is fully inserted into said cannula, said tip extends beyond said narrowing open tip of said cannula for lateral shifting of tendons and nerves from a path thereof as said cannula with said obturator fully inserted therein is passed in the carpal tunnel.

8. A combination according to claim 7, said cannula grip having means fixed thereto for providing visual indication of an angular orientation of said slot when said cannula is fully inserted into the carpal tunnel.

9. A combination according to claim 8, said tube having a matted interior surface.

10. A combination according to claim 7, said cannula tip and said obturator tip having smoothly converging surfaces when said obturator is fully inserted into said cannula.

11. For use in endoscopic carpal tunnel surgery, a combination of instruments comprising:

a cannula having an elongated tube of diameter suitable for passage in the carpal tunnel, said tube defining a first instrument passage longitudinally therein and having a grip fixed to a rear end thereof, said cannula grip having a second instrument passage extending therethrough and aligned with said first instrument passage, and an elongated longitudinal slot extending from a point proximate a forward end of said cannula grip to a point proximate a diametrically narrowing open tip at another end thereof; and a rasp having an elongated rod of diameter suitable for passage in said cannula, said rod having a grip fixed to a rear end thereof and a tip having a roughened upper face on a forward end thereof, said face having a width less than a width of said longitudinal slot in said cannula, said tip having an upwardly tapering trapezoidal cross-section taken transversely to a longitudinal axis of said rod for guiding penetration of said tip through said longitudinal slot in said cannula, a base of said trapezoidal cross-section being greater than said width of said slot in said cannula for limiting penetration of said tip therethrough.

12. A combination according to claim 11, said grip having means fixed thereto for providing visual indication of an angular orientation of said slot when said cannula is fully inserted into the carpal tunnel.

13. A combination according to claim 11, said tube having a matted interior surface.

14. For use in endoscopic carpal tunnel surgery, a combination of instruments comprising:

a cannula having an elongated tube of diameter suitable for passage in the carpal tunnel, said tube defining a first instrument passage longitudinally therein and having a grip fixed to a rear end thereof, said cannula grip having a second instrument passage extending therethrough and aligned with said first instrument passage, and an elongated longitudinal slot extending from a point proximate a forward end of said cannula grip to a point proximate a diametrically narrowing open tip at another end thereof; and a rasp having an elongated rod of diameter suitable for passage in said cannula, said rod having a grip fixed to a rear end thereof and a tip having a toughened upper face a forward end thereof, said face having a width less than a width of said longitudinal slot in said cannula, said tip having an upwardly tapering trapezoidal cross-section taken transversely to a longitudinal axis of said rod for guiding penetration of said tip through said longitudinal slot in said cannula, said rod being bent to provide forward and rearward segments having displaced parallel longitudinal axes.

15. A combination according to claim 14, said rod being bent proximate a midpoint thereof.

16. A combination according to claim 14, said displacement being such that, when said rearward segment is substantially concentrically aligned within said cannula, said roughened upper face is external of said cannula.

* * * * *